United States Patent [19]

Theisz

[11] Patent Number: 4,883,045

[45] Date of Patent: Nov. 28, 1989

[54] METHOD FOR CONTROLLING GROWTH OF TISSUE CELLS

[76] Inventor: Erwin Theisz, 127 Randolph Rd., White Plains, N.Y. 10607

[21] Appl. No.: 122,627

[22] Filed: Nov. 19, 1987

Related U.S. Application Data

[63] Continuation of Ser. No. 780,414, Sep. 26, 1985, abandoned.

[51] Int. Cl.$^4$ ............................................. A61H 1/00
[52] U.S. Cl. ...................................... 128/24 A; 604/25
[58] Field of Search ......................... 128/24 A; 604/25

[56] References Cited

U.S. PATENT DOCUMENTS

| | | | |
|---|---|---|---|
| 1,146,292 | 7/1915 | Wappler | 604/25 |
| 2,132,539 | 10/1938 | McRae | 604/25 |
| 3,117,571 | 1/1964 | Fry | 128/24 A |
| 4,227,894 | 10/1980 | Proynoff | 55/126 |
| 4,305,390 | 12/1981 | Swartz | 604/24 |

FOREIGN PATENT DOCUMENTS

| | | | |
|---|---|---|---|
| 468632 | 9/1975 | U.S.S.R. | 128/24 A |
| 648234 | 2/1979 | U.S.S.R. | 128/24 A |
| 825073 | 5/1981 | U.S.S.R. | 128/24 A |
| 884700 | 11/1981 | U.S.S.R. | 128/24 A |
| 910157 | 3/1982 | U.S.S.R. | 128/24 A |
| 436257 | 10/1935 | United Kingdom | 604/25 |

OTHER PUBLICATIONS

"Research in Cancer Therapy with Ultrasound", IEEE, pp. 142-147, 1977.
Martin, "Climate Control Through Ionization", Journal of the Franklin Institute, vol. 254, No. 4, pp. 267-280.
Eddy et al., "The Effect of Negative Ionization on Transplanted Tumors", Cancer Res., vol. 11, No. 4.

*Primary Examiner*—David A. Wiecking
*Assistant Examiner*—Aaron J. Lewis
*Attorney, Agent, or Firm*—Cohen, Pontani & Lieberman

[57] ABSTRACT

A method for controlling the growth of tumorous tissue in mammals such as humans and more particularly a method for inhibiting the growth of tumorous cells is provided by exposing the subject to an atmosphere of increased negative ion concentration and by preferably simultaneously exposing the afflicted tissue to ultrasonic vibration.

4 Claims, No Drawings

METHOD FOR CONTROLLING GROWTH OF TISSUE CELLS

This is a continuation of U.S. application Ser. No. 780,414, filed Sept. 26, 1985, now abandoned.

TECHNICAL FIELD

This invention pertains to a method for controlling the growth of tissue cells, such as tumorous tissue cells, and more specifically to the remission and/or substantial removal of tumorous cells by the application of ion inhalation and ultrasonic vibration.

BACKGROUND ART

A tumor is an autonomous new growth of tissue of an unknown single, specific cause. Tumors possess the structure of the body tissue or organ in which they originate, exhibit unlimited and uncontrolled power of growth and have the ability and tendency to spread and metastasize to distant locations where they may lodge and assume a renewal of growth. Tumor cells grow by multiplication of the individual's own tissue cells, are endowed with tremendous growth energy and largy lack the growth restraint which characterizes normal healthy tissue.

The invention disclosed and claimed herein pertains generally to a method for inhibiting the growth of tumorous tissues in mammals, such as humans, by the application of ultrasonic vibration and negative ion inhalation. Various methods of disintegration or destruction of tumor cells are known. For example, U.S. Pat. No. 4,343,301 discloses a method and apparatus for a non-invasive high energy low frequency wave for destroying tumors through local heating. Other examples of tissue disintegration by thermal heating are given in U.S. Pat. Nos. 3,958,559; 3,237,623 and 3,117,571.

Other known ultrasonic techniques in which the probe is surgically inserted into the patient are disclosed in U.S. Pat. Nos. 4,136,700; 4,063,557; 3,896,811; 3,823,717; 3,805,787; 3,585,363; 3,565,062 and 3,352,303.

U.S. Pat. No. 4,315,514 discloses a method for the destruction of abnormal cells based on the difference of structure between normal tissue cells and abnormal cells and the different frequencies thereof.

At present, various techniques are available for ionizing air for reasons of dust removal and possible biophysiological effects such as the improvement of pyschomotor performance and response. U.S. Pat. Nos. 3,534,530; 3,483,672 and 3,311,108 typically disclose devices for producing and controlling electric fields by sealing-mounted or self-contained electrode arrangements.

DISCLOSURE OF THE INVENTION

Tumor cells exhibit unlimited and uncontrolled growth together with the ability and tendency to metastasize and spread to distant locations where they may lodge and assume renewal of growth. It has now been found that such unlimited and uncontrolled growth of tumorous cells may be inhibited by the application of ultrasonic vibration and negative ion inhalation. The treatment with negative ions is believed to raise. The electric potential of the cells to the level of a healthy normal cell which lies generally between about $-75$ mV to about $-90$ mV. The pH value of the blood serves as an indication of the cell potential. An acidic pH is indicative of a positive charge, while alkaline conditions indicate a negative charge. The negative ion treatment thus serves to maintain the desired cell potential and to maintain the blood at alkaline conditions. At the same time, negative ions stimulate the oxidation of seretonin, a powerful neurohormone which absorbs oxygen by monoamine oxidation. Through additional administration of specific ultrasonic frequencies, the healthy cell reactions are accelerated and undesirable debris and toxins are removed from the system.

Thus, the present invention pertains to a method for inhibiting the growth of tumorous tissue in mammals such as humans, whereby the patient is exposed to an atmosphere of increased negative ion concencentration for a limited treatment period as to cause the electric potential of the cell to be restored to a healthy level and whereby the patient is preferably simultaneously exposed to ultrasonic vibrations for at least a portion of the treatment period. By raising the electric potential of the afflicted cell to that of a normal cell, uncontrolled cell division characteristic of a tumorous tissue condition is blocked.

DETAILED DESCRIPTION OF THE PREFERRED EMBODIMENTS

It has now been found that unarrested cell growth, characteristic of tumorous conditions, can be substantially arrested or inhibited by subjecting the patient to application of negative ion inhalation and ultrasonic vibration. Preferably, both treatments are applied simultaneously.

Although the exact scientific principles on which this invention is based on are, at present, not fully understood, the following description does reflect the present understanding of the underlying scientific theories. Of course, it is understood that this invention is not limited to any such theory.

It is known that the concentration of potassium ions within a living cell is higher than the concentration of sodium ions outside the cell. On the other hand, the concentration of sodium ions within the living cell is substantially lower than the concentration of potassium ions, while outside the cell, there exists a much higher sodium ion concentration. Characteristically, a normal cell has a negative charge. The high concentration of positive potassium ions within the cell causes a negative charge or negative electric potential on the inside wall of the cell membrane. However, when the ion concentration is greater on the outside of the cell, the charge or electric potential inside the cell is lowered. To maintain a high negative cell potential, the potassium ion concentration within the cell must therefore be greater than the sodium ion concentration outside the cell. Determination of this physical phenomenon is generally accomplished by pH measurement of the blood.

Typically, the negative ion treatment uses charged oxygen as the negative ion in the presence of nitrogen and water vapor as they exist in ambient air. The ejected electron from the negative ion generator can attach itself to oxygen, water vapor or dirt particles in the air to produce the ions, or it can attach itself to any non-toxic electro-negative gas, but oxygen is preferred. A room or direct pulmonary intake of negative ions may be conditioned with a predetermined negative ion concentration which typically may be at average levels of about 2,000 to about 12,500 ions/cm$^3$. A level of negative ion concentration of about 10,000 ions per cm$^3$ is particularly preferred.

The exposure times may vary but are typically about ten hours per day over a treatment period of about ten to about fourteen days. Typically, the patient will be exposed and thereby inhale a moderate negative ion concentration of about 10,000 ions/cm$^3$ for eight hours per day over a ten-day period or 480 minutes per day applied in two sequences.

The negative ions may be generated by a commercially available negative ion generator, e.g. marketed by Ion Research Center, 14670 Highway 9, P.O. 905, Boulder Creek, Calif. 95006 or by Emerson Electric Ion Generator or Generators from Simco Co. Inc., Landsdale, Pa.

In such units, an ultraviolet lamp is used to generate the negative ions. The ions are generated within an enclosure and brought into the room or treating environment by means of an exhaust fan at the end of the enclosure or box. A shield plate serves as an ion trap to prohibit the movement of positive ions into the treating environment so as to result in an enhanced negative ion concentration in the air. Preferably, the ion generator is located near a low-speed fan which provides a gentle mixing of the ions with the air of the treating environment. The relative ion concentration can be monitored by measuring the ion flow between the plates of a concentric tube polarized capacitor through which the ionized air is drawn at a constant flow rate. The ion flow can be measured and recorded with a commercially available electrometer such as the Keithly Electrometer Model 600A.

A negative ion generator is generally required to reach the desired level of negative ion concentration, but sufficient negative ions may be also found in nature as a result of natural phenomena. Thus, energy from cosmic rays and ultraviolet radiation acting on clean air may result in up to 4,000 ions/cm$^3$.

Although negative ion treatment alone results in a substantial remission of tumor growth, the subject is preferably exposed to ultrasonic vibration simultaneously with the negative ion treatment. The ultrasonic vibration may be applied locally directly to the site of the tumor tissue, and may include application to the tissue adjacent the tumor.

Pulsed ultrasonic vibration is particularly important where large grown tumors are present since the existing tumor protein is decomposed or liquified. Moreover, the application of pulsed ultrasonic energy produces an electric charge due to the friction between the resonating cavities and the surrounding liquid so as to build up the negative electrostatic potential required for healthy cells. In addition, the application of particular ultrasonic frequencies will stimulate and initiate chemical reactions necessary to the health of the cells. Deleterious and unwanted bacteria and other microorganisms are also destroyed by ultrasonic radiation of sufficient intensity and specific frequency.

It is also possible to inhibit or retard virus penetration of the cell in cases of viral diseases, simply by activating the defense mechanism of the cell by specific vibrational frequencies. In addition, the tumorous cell "sarcoma" can be disintegrated and broken up into smaller size debris which is easily eliminated by the system. While gamma ray or X-ray treatment may destroy the life of a cell, it is unable to disintegrate or dissolve the afflicted cell into removable debris. An effective tumor treatment is thus provided by raising the cell potential through a pH change by negative ion intake and by the preferably simultaneous administration of specific ultrasonic frequencies to accelerate the reaction and to dissolve or liquify undesirable cell debris and toxins from the system.

Suitable levels of ultrasound intensity are from about 0.2 to about 1.5 w/cm$^2$. Generally, ultrasonic frequencies of about 500 to about 1,000 KHz, for exposure periods of about 8 to about 25 minutes, preferably about 25 minutes, are employed.

Standard commercially available equipment for the application of ultrasonic treatment to the patient's body may be utilized. A suitable unit is the Medco-Sonlator, manufactured by Medco Products Company, Inc., 3601 E. Admiral Close, Tulsa, Okla. 74150. Other suitable ultrasonic units are the Siemens Ultratherm 608, distributed by General Theraphysical Inc. at 2018 Washington Avenue, St. Louis, Mo. and The Ultrasound Mark IV (1,000 KHz and 20 Watts/cm$^2$) from Rich-Mar Corp., Tulsa, Okla.

The various aspects and modifications of the present invention will be made more clearly apparent by reference to the following examples which are understood to be illustrative only and in no way limititive of the present invention.

EXAMPLE 1

A subject having a tumorous condition such as a tumor of the skin is placed in a room containing water vapor and nitrogen at customary ambient levels, and is exposed to a negative ion concentration of about 10,000 ions/cm$^3$. The negative ion concentration in the room is maintained and the patient thereby inhales the negative ions for an alternated period of 10 hours treatment for about 3 to about 10 days.

During the period of negative ion inhalation, ultrasonic vibration is locally applied to the tumorous area at a frequency of about 800 KHz for approximately 10 to 15 minutes.

EXAMPLE 2

A single white mouse with two skin tumors, i.e. dorsal and lateral carcinoma, in the form of histologically verified squamous cell carcinoma of the skin, and additionally one papilloma located near the dorsal tumor was exposed to approximately 10,000 negative ions/cm$^3$ during daytime hours for four spaced two hours treatment periods each day for two days. This treatment was applied to both, the dorsal and lateral carcinomas and the papilloma. After the second day, the treatment for all three tumors, dorsal and lateral carcinoma and papilloma, included constant daytime application of negative ions from the third day on during the treatment period set forth below. At no time during this treatment period was exposure to negative ions provided during nighttime hours. Additionally, ultrasonic treatment was applied during the treatment period from the sound head of the ultrasonic unit which measured two inches inside diameter. This sound head was passed above the tumor and papilloma for 25 minutes, once per day at 1,000 KHz in overlapping parallel strokes covering ¼ inch per minute without pressure or friction. A conductivity gel such as Lectron II was used as a coupling agent. Ten minutes additional ultrasonic vibrational treatment was applied for the tumors and papilloma on the third day.

The treatment period for the dorsal tumor was 60 days which included 8 hrs/day of negative ion inhalation and 25 minutes of ultrasonic vibrational treatment for the first three days. The treatment period for the lateral tumor was 60 days with respect to negative ion inhalation and 25 minutes with respect to ultrasonic vibration which, however, did not begin until approximately three weeks after the initial negative ion treatment. The treatment period for the papilloma lasted only twelve days with respect to the negative ion inhalation and 25 minutes with respect to the ultrasonic vibration treatment.

Almost immediately after the first ultrasonic exposure, the dorsal tumor was partially swollen and its healthy surroundings showed a light redish color with a light indentation. After fifteen days, the appearance of the dorsal tumor changed, the dorsal tumor then began to heal and a light indentation was visible in the center of the tumor while the edge thereof remained hard. The healthy surroundings of the dorsal tumor began to loosen up from the base. After the application of additional ultrasonic vibration on the third day of the treatment period, the tumor showed steady healing with a tender scar formation.

The lateral tumor was allowed to grow to a full sized tumor before ultrasonic vibration began. The tumor was large, inflamed and deeply rooted in the side muscles of the right rear leg of the mouse and was interwoven with healthy tissue. The top surface of the tumor was flat. The skin of the tumor was thin, but taut and shiny. The back corner of the tumor showed a fresh excision spot. Shortly after the ultrasonic vibration treatment began, the tumor showed a swollen reaction. The surface was grayish/white and excretion of a viscous paste was observed. Two days later, the tumor was still swollen, but softer in appearance. It was covered with a very thin layer of fine tissue and showed no ulceration. One week later, the entire lateral tumor except for a small crust covered area, had a healthy appearance. At certain points under the crust, a secretion was observed. Approximately one month later, the tumor was completely separated from the base and in its place, there was a fine scar with a light indentation in the center.

The papilloma located near the dorsal tumor showed a complete fragmentation within ten days after treatment began. The fragmentation was covered with a fine tissue layer and complete healing took place within two days thereafter.

EXAMPLE 3

Five black mice suffering from implanted Ridgeway Ostoegenic Sarcoma (ROS) received the identical treatment described in Example 2 with respect to the dorsal tumor, except the four two-hour negative ion inhalation treatment periods per day lasted eight days rather than two days. All five black mice afflicted with Ridgeway near the kidneys showed considerable growth of the tumors within ten days after implantation. The size of the tumors were approximately the size of a bean. The growth of the tumors ceased at approximately the 15th day after treatment began and the tumors which measured one and ½ inches by ½ inch fell out . on the 18th day after application of the ultrasonic treatment.

EXAMPLE 4

Three black mice suffering from Ridgeway Osteogenic Sarcoma (ROS) were treated with the negative ion generator only, without the use of ultrasonic vibration. The procedure of the negative ion treatment with respect to the dorsal tumor of Example 2 was followed resulting in a retardation of the tumor development. A tumor growth delay of approximately five days was indicated.

EXAMPLE 5

Three black mice suffering from Ridgeway Osteogenic Sarcoma (ROS) received the negative ion treatment described with respect to the dorsal tumor in Example 2. The ultrasonic vibration of Example 2 was followed with the exception that only three exposures at the rate of one per day for 25 minutes were applied. A further retardation in the tumor growth of approximately five days was observed.

EXAMPLE 6

In the following example (Test A, below), seven $AKD_2F_1$ black mice afflicted with Ridgeway Osteogenic Sarcoma (ROS) received only treatment with negative ions.

On the seventh day after treatment began, the tumor of the $AKD_2F_1$ mice stopped growing and regressed, and after three weeks, the tumor was completely eliminated without reoccurrence after the twenty-first day. Even when reinjected with a new tumor, reoccurrence of the tumorous growth was not observed.

The therapy was performed under the same conditions (10,000 ions/$cm^3$ for 8 hrs/day) in tests B through E by using four test cages containing ten $AKD_2F_1$ mice each. Four times ten mice served as controls. The result of these tests are shown in Table I:

TABLE I

| Test No. | $AKD_2F_1$ black mice - tumor donor - "ostogenic Sarcoma ROS", | | |
|---|---|---|---|
| | No. of Days Of Treatment | Control Size Of Tumor | Experiment Size Of Tumor |
| Test A | 11 | 100% | 61% remission |
| | 18 | 100% | 24% remission |
| | 21 | 100% | COMPLETELY ELIMINATED |
| TEST B | 18 | 100% | 24% remission |
| TEST C | 21 | 100% | 16.56% remission |
| TEST D | 24 | 100% | 73% remission |
| TEST E | 27 | 100% | 51.1% remission |

EXAMPLE 7

Ten hybrid mice $BDF_1$ implanted with S-180 were treated with simultaneous negative ion/ultrasonic vibration theraphy. The results of the treatment are given Table II.

TABLE II

| | HYBRID MICE $BDF_1$ (S-180) | | |
|---|---|---|---|
| Test No. | No. of Days Of Treatment | Control Size Of Tumor | Experiment Size Of Tumor |
| TEST F | 11 | 100% | 49.5% remission |
| TEST G | 18 | 100% | 68% remission |

EXAMPLE 8

Ten $AKD_2F_1$ black mice afflicted with Ridgeway Osteogenic sarcoma (ROS) were treated as described with the combined negative ion/ultrasonic vibration treatment (10,000 ions/$cm^3$, 8 hrs/day about 1000 Hz).

The results are set forth in Table III.

TABLE III

AKD$_2$F$_1$ BLACK MICE - SOLID TUMOR DONOR
"OSTOGENIC SARCOMA ROS"

| Test No. | No. of Days Of Treatment | Control Size Of Tumor | Experiment Size Of Tumor |
|---|---|---|---|
| TEST H | 21 | 100% | 45% remission |
| TEST I | 24 | 100% | 70.2% remission |
| TEST J | 27 | 100% | 41.2% remission |

EXAMPLE 9

Ten hybrid male mice BDF$_1$ (S-180) were treated as described in Example 2. Ten control mice were left untreated. After eleven days of treatment, the tumor of the treated mice decreased to about 45% of that of the control mice. The control mice had developed large tumors and died after eleven days of the experiment. The tumor of the treated animals continued to decrease.

Those skilled in the art will appreciate that the preferred method of the invention as described hereinabove may be modified once this description is known. For example, the combined treatment may include negative ion inhalation at a concentration of up to 20,000 ions/cm$^3$ and instead of the described one, it may comprise two ultrasonic vibration treatment periods.

Since these as well as other changes and modifications are intended to be within the scope of the present invention, the above description should be construed as illustrative only and not in a limiting sense, the scope of the invention being defined by the appended claims.

What is claimed is:

1. A method for inhibiting the growth of tumorous tissue in a mammal, comprising:
    (a) exposing the mammal to an atmosphere of increased negative ion concentration of about 10,000 ions/cm$^3$ for a treatment period sufficient for causing the cell potential to be restored to healthy levels and
    (b) simultaneously exposing the afflicted tissue to ultrasonic vibrations at a frequency of about 1,000 KHz for at least a portion of the treatment period, for about 25 minutes per day during said treatment period.

2. The method of claim 1, wherein the cell potential is restored to a range from about $-75$ to $-90$ mV.

3. The method of claim 1, wherein the negative ion comprises negatively charged oxygen.

4. The method of claim 2, wherein the negative ion comprises negatively charged oxygen.

* * * * *